(12) United States Patent
Ng et al.

(10) Patent No.: US 11,834,620 B2
(45) Date of Patent: Dec. 5, 2023

(54) CENTRIFUGE ENERGY HARVESTING CHAMBER

(71) Applicant: The Hong Kong University of Science and Technology, Hong Kong (CN)

(72) Inventors: Charles Wang Wai Ng, Hong Kong (CN); Sina Baghbanrezvan, Hong Kong (CN)

(73) Assignee: The Hong Kong University of Science and Technology, Hong Kong (CN)

(*) Notice: Subject to any disclaimer, the term of this patent is extended or adjusted under 35 U.S.C. 154(b) by 50 days.

(21) Appl. No.: 17/527,608

(22) Filed: Nov. 16, 2021

(65) Prior Publication Data

US 2022/0154091 A1 May 19, 2022

Related U.S. Application Data

(60) Provisional application No. 63/205,107, filed on Nov. 16, 2020.

(51) Int. Cl.
*B01J 3/04* (2006.01)
*C10L 3/10* (2006.01)
*B01J 19/18* (2006.01)

(52) U.S. Cl.
CPC .............. *C10L 3/108* (2013.01); *B01J 3/04* (2013.01); *B01J 19/1806* (2013.01); *B01J 2219/00069* (2013.01)

(58) Field of Classification Search
CPC ......... B01J 3/04; B01J 19/1806; C10L 3/108; E21B 43/01
See application file for complete search history.

(56) References Cited

U.S. PATENT DOCUMENTS 5,634,876 A 6/1997 Schofield
5,783,760 A * 7/1998 Haines ............... G01N 15/0806
73/865.6
(Continued)

FOREIGN PATENT DOCUMENTS

CN 1440832 A 9/2003
CN 101575964 A 11/2009
(Continued)

OTHER PUBLICATIONS

Feng, J.- C., et al., "Large Scale Experimental Evaluation to Methane Hydrate Dissociation below Quadruple Point by Depressurization Assisted with Heat Stimulation," Energy Procedia, 2017, 142:4117-4123.
(Continued)

*Primary Examiner* — Lessanework Seifu
(74) *Attorney, Agent, or Firm* — Saliwanchik, Lloyd & Eisenschenk

(57) ABSTRACT

Systems and methods related to centrifuge energy harvesting chambers (CEHCs) for gas production simulation are provided. Certain CEHCs may include a high-pressure chamber, high-pressure syringe pumps, cooling systems, an actuator and surcharge, backpressure control inside the wellbore, a heating element on the wellbore, water gas separation systems, and flow measurement systems. Certain CEHCs may also provide software operably connected to sensors and instrumentation, comprising a module to continuously, in real-time, periodically, or asynchronously, measure and monitor simulation variables.

20 Claims, 8 Drawing Sheets

(56) References Cited

U.S. PATENT DOCUMENTS

| | | | |
|---|---|---|---|
| 9,598,936 | B1 | 3/2017 | Gao et al. |
| 9,790,743 | B2 | 10/2017 | Li et al. |
| 9,841,531 | B2 | 12/2017 | Li et al. |
| 10,095,819 | B2 | 10/2018 | Li et al. |
| 10,408,728 | B2 | 9/2019 | Li et al. |
| 11,187,691 | B2 * | 11/2021 | Zhu .................... E21B 43/01 |
| 2016/0251943 | A1 | 9/2016 | Li et al. |

FOREIGN PATENT DOCUMENTS

| | | |
|---|---|---|
| CN | 101963057 A | 2/2011 |
| CN | 107063789 A | 8/2017 |
| CN | 109633754 A | 4/2019 |

OTHER PUBLICATIONS

Wang, Y., et al., "A three-dimensional study on methane hydrate decomposition with different methods using five-spot well," Applied Energy, 2013, 112:83-92.

Konno, Y., et al., "Experimental evaluation of the gas recovery factor of methane hydrate in sandy sediment," RSC Advances, 2014, 4:51666-51675.

Kwon, T.- H., et al., "Geomechanical and Thermal Responses of Hydrate-Bearing Sediments Subjected to Thermal Stimulation: Physical Modeling Using a Geotechnical Centrifuge," Energy & Fuels, 2013, 27:4507-4522.

Heeschen, K.U., et al., "Gas Production from Methane Hydrate: A Laboratory Simulation of the Multistage Depressurization Test in Mallik, Northwest Territories, Canada," Energy & Fuels, 2016, 30:6210-6219.

* cited by examiner

Section BB

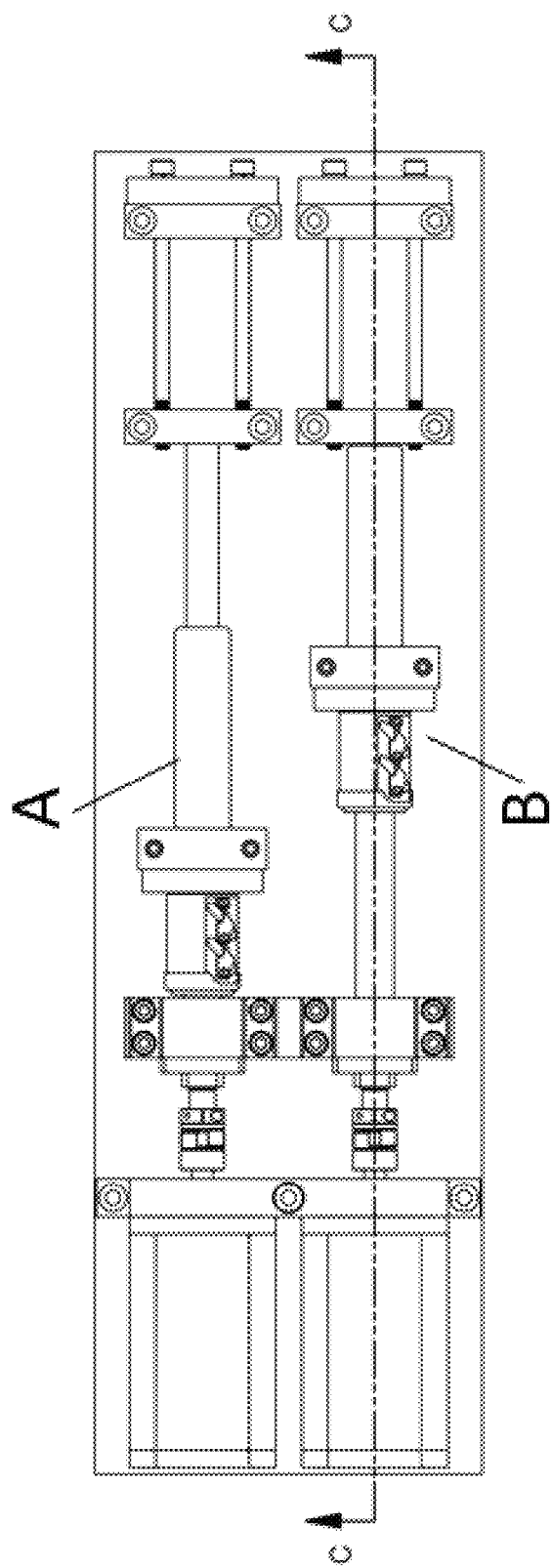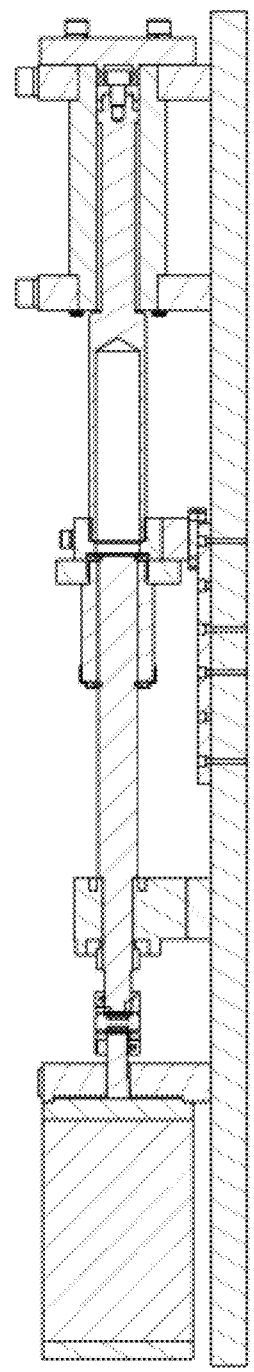
FIG. 4D
FIG. 4E

CENTRIFUGE ENERGY HARVESTING CHAMBER

CROSS-REFERENCE TO RELATED APPLICATION

This application claims the benefit of U.S. Provisional Application Ser. No. 63/205,107, filed Nov. 16, 2020, which is hereby incorporated by reference in its entirety including any tables, figures, or drawings.

BACKGROUND

The subject invention is concerned generally with the field of gas production from hydrate-bearing sediments and specifically with experimental devices and methods for simulating hydrate-bearing sediment-structure interactions or problems.

There exist several proprietary devices for simulating gas production from hydrate-bearing sediments. Many of these devices consist of a high-pressure chamber and a cooling unit for sustaining favorable pressures and temperatures for gas hydrate formation, a back pressure regulator setup for decreasing the wellbore pressure, a gas/water separator, and flow measurement devices. In many existing devices the effective stress, which governs the soil behavior, is either ignored or imposed through isotropic or one-dimensional surcharge loading to the sediments. Hence, the stress gradient is not imposed on soil during depressurization tests. Furthermore, the proprietary devices fail to impose correct pressure boundaries by a continuous flux high-pressure fluid. Hence, the whole chamber is depressurized at once and the localized dissociation in the vicinity of the wellbore as well as the pressure field evolution during the gas production is not captured. Consequently, the induced stresses on the wellbore casing are not simulated correctly.

U.S. Pat. No. 5,634,876 issued to Schofield, discloses centrifuges and associated apparatus and methods. Geotechnical centrifuge testing is a common advanced physical modelling method to investigate soil-structure interaction problems as well as global soil behavior. One method to approximate the actual field stress gradient is to use a geotechnical centrifuge, which is a powerful and economical physical modelling tool to simulate and evaluate deformation and failure mechanisms of stress-dependent problems such as slope stability and gas exploitation in deep waters. Furthermore, a geotechnical centrifuge can expedite the solution of time-dependent problems through the scaling laws associated with centrifuge modelling. It is well-known that hydrate dissociation is a time-dependent process influenced by both conduction and convection of heat. Since existing devices are not designed to operate at an elevated effective field of gravity (e.g., as produced by a geotechnical centrifuge) where the time of the heat transfer through conduction and convection is scaled, the long-term production behavior of gas hydrate-bearing sediments is not captured by these existing devices. There exists therefore, a need to develop and design equipment for simulating gas hydrate dissociation, which can be used in a geotechnical centrifuge environment.

BRIEF SUMMARY

As a potential source of energy for the future, methane hydrates are the most commonly occurring gas hydrates and are typically found in permafrost and marine soil sediments. The subject invention provides systems and methods useful to investigate the behavior of these sediments through physical models in the laboratory to develop more reliable gas extraction methods from these sediments and ensure the safety of offshore infrastructures.

Embodiments of the subject invention provide a centrifuge energy harvesting chamber (CEHC) that allows improved simulation of the interactions between hydrate-bearing sediments, wellbore casings, and offshore structures. Embodiments are advantageously configured and adapted to sustain the required temperature and pressure conditions for hydrate stability at an elevated gravity environment of the geotechnical centrifuge. In one particular embodiment, for example, two sets of syringe pumps may be designed to generate continuous flux conditions at the boundaries resulting in sustaining of the stability pressures at the boundaries during hydrate dissociation. To simulate dissociation induced by depressurization in-flight (during operation of, or under pressure from, the centrifuge), a configurable or programmable back pressure regulator may be used and controlled by computer software, electronic controls, or other methods known in the art. To simulate a thermal stimulation method with depressurization, a heating element may be installed inside the wellbore. The produced gas and water can be separated by a gas/water separator. A built-in actuator can impose surcharge loading on the sediment or working load on the offshore structures. Thus, the CEHC may be configured as a standalone unit that can simulate different gas production methods in-flight and evaluate or predict the induced forces on the production casing wellbore and offshore structures during future gas production in the field Embodiments of the subject invention may provide an apparatus, method, and system for an energy harvesting chamber to be used in a high-g centrifuge environment (e.g., up to 100 times the gravity of the Earth, or about 100 times the gravity of the Earth, or more than 100 times the gravity of the Earth) that allows simulation of hydrate dissociation, wellbore casing deformation, seabed subsidence during gas production from hydrate-bearing soils and $CO_2$ sequestration. Certain embodiments may be used for even higher capacity of pressures, temperatures, or high-gravity forces by modifying the design of the chamber for higher factor(s) of safety. Certain embodiments of the subject invention provide a chamber that can operate at an elevated gravity environment (e.g., up to 100 times the gravity of the Earth corresponding to 100 m typical gas hydrate sediments in nature) of the centrifuge with the capability of sustaining the thermodynamically favorable conditions for hydrate formation (e.g., temperatures of −10 to 15 degrees Celsius and pressures of up to 16 MPa, which are typical temperature and pressure ranges for the marine and permafrost hydrate bearing sediments), sustaining a continuous inflow of high-pressure water (inflow of 2000 $cm^3$/min at 12 MPa pressure) at the boundaries during the dissociation and an in-flight measurement and control of parameters including gas and water injection pressures, shear and P-wave wave velocities measurement, electrical resistivity and axial and bending strain measurements in the wellbore, wellbore pressure of 0.5 MPa and surcharge loading of up to 3 MPa.

BRIEF DESCRIPTION OF DRAWINGS

Some embodiments of the present invention are illustrated as an example and are not limited by the figures of the accompanying drawings, in which like references may indicate similar elements and in which:

FIGS. 4A-4E illustrate an embodiment of continuous flux high-pressure syringe pumps at fully retracted and fully extended conditions in accordance with an embodiment of the subject invention.

DETAILED DESCRIPTION

Figure 1:
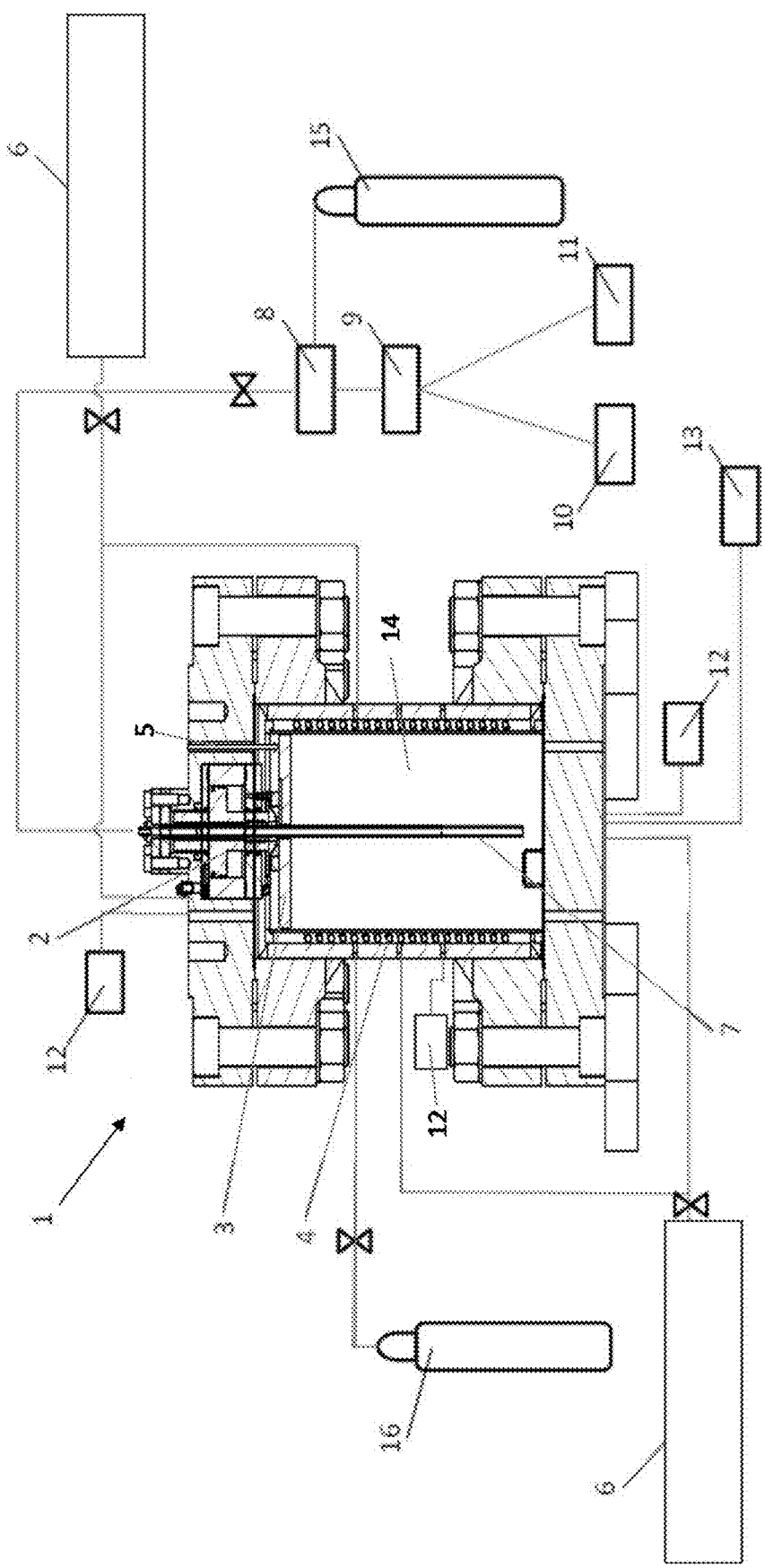
FIG. 1 illustrates a centrifuge energy harvesting chamber (CEHC) setup and selected associated components in accordance with an embodiment of the subject invention.

FIG. 1 shows an exemplary CEHC setup and associated components for a gas production simulation in accordance with an embodiment of the subject invention. It consists of 1) a high-pressure chamber 1 to sustain the required pressure for hydrate formation (up to 16 MPa) inside the sediment 14; 2) high-pressure pumps (e.g., one or more syringe pumps) 6 to generate the required pore pressures for hydrate formation as well as sustaining the pressure at the boundaries during dissociation, and pressure transducers 12 at the boundaries to measure the water pressure and gas pressure from gas cylinder 16; 3) cooling system comprising built-in cooling coil 4 inside the high-pressure chamber and a circulating bath with the cooling capacity of 4000 W at 0° C. 13 outside the chamber to sustain the temperatures for hydrate formation and stability; 4) a built-in hydraulic actuator 2 and surcharge plate 3 to simulate the surcharge loading; 5) Back pressure control unit the pressure control range of 10 to 30000 kPa 8 and N2 gas cylinder 15 to control the pressure inside the wellbore (e.g., 10-10000 kPa) 7, a heating element on the wellbore, water gas separation system 9, and flow measurement systems for gas 10 and for water 11.

Embodiments may provide software operably connected to sensors and instrumentation, comprising a module to continuously, in real-time, periodically, or asynchronously, measure and monitor variables, including for example variables related to the backpressure regulator and the pumping rate. The sensors used in the invention may further include but are not limited to temperature, pore pressure 12, bender elements, displacement 5, strain gauge sensors, and other sensors or measurement devices and systems known in the art.

Figure 2:
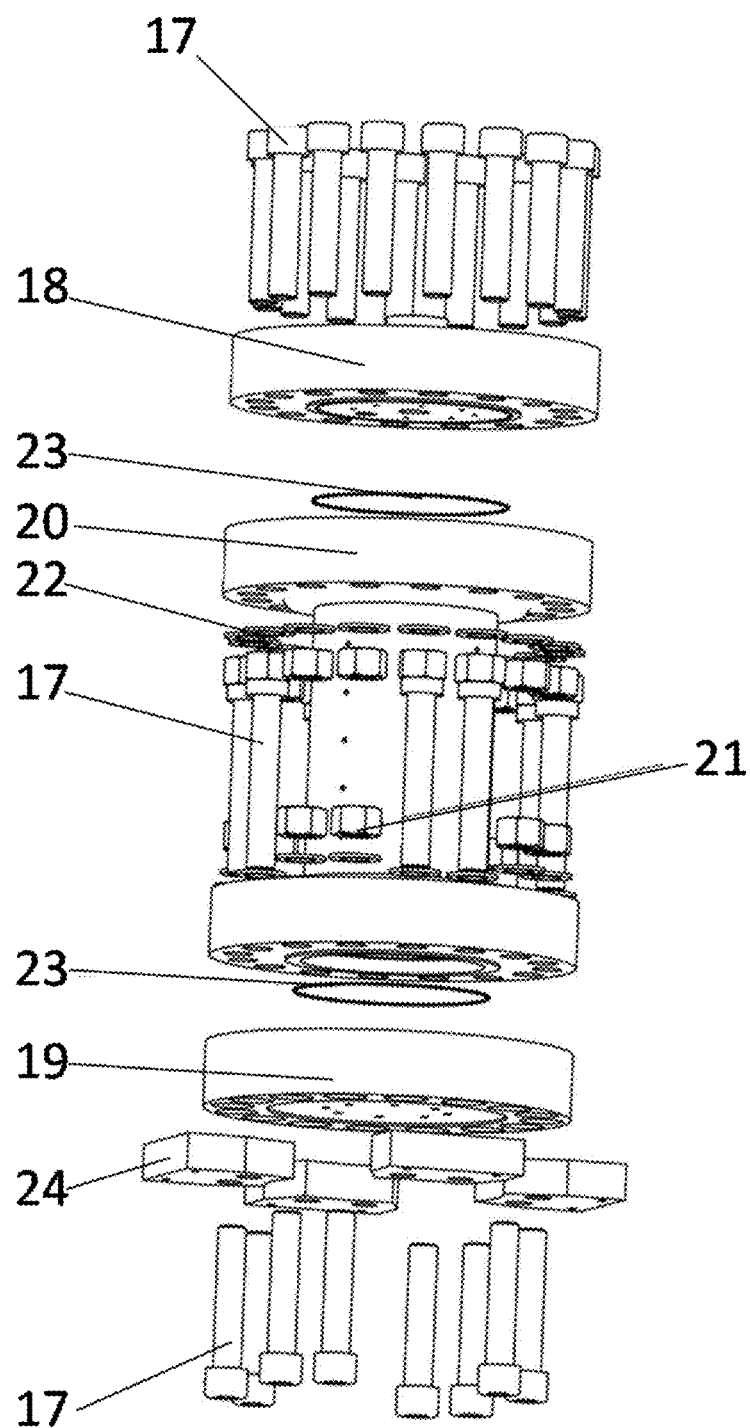
FIG. 2 illustrates an exploded view of an assembly of major structural components of the CEHC in accordance with an embodiment of the subject invention.

FIG. 2 illustrates selected major structural components of a high-pressure chamber of a CEHC according to an embodiment of the subject invention. The CEHC may include one or more of a chamber cylinder weldment 20, top instrumentation disk 18, bottom instrumentation disk 19, chamber feet 24, bolts 17, nuts 21, washers 22, and sealing O-rings 23. While the specific exemplary embodiment shown in FIG. 2 may have certain beneficial advantages (e.g., strength, compactness to be used on geotechnical centrifuge, manufacturability, and reliability) the elements may be arranged as shown or in alternative configurations to beneficial effect. For example, in certain embodiments, sealing O-rings 23 may be replaced by a different type, number, arrangement, or placement of sealing elements; more or fewer bolts and nuts of differing sizes may be used; rivets, weldments, snap-rings, or other fasteners may be substituted to meet design constraints and criteria; chamber feet 24 may be of individual, grouped (e.g., 2 or more manufactured together), or unitary construction; elements or functions of chamber cylinder weldment 20, top instrumentation disk 18, or bottom instrumentation disk 19 may be grouped together or separated. Many such changes may remain within the subject invention while using alternative detailed component designs or assembly methods resulting in the same, more, or fewer parts required to complete a given embodiment.

Figure 3A:
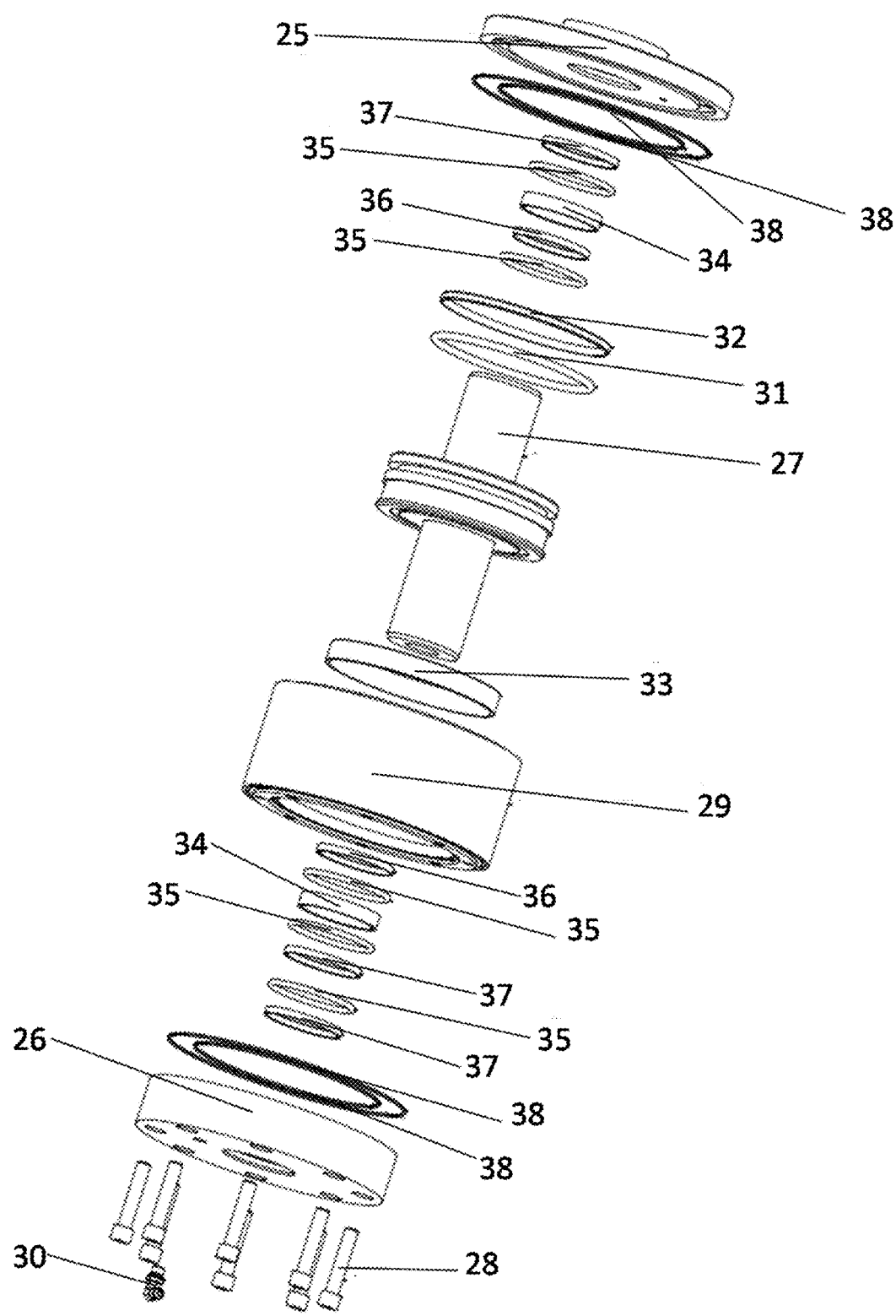
FIGS. 3A-3C illustrate an assembly of a built-in actuator in a CEHC in accordance with an embodiment of the subject invention.
Figure 3B:
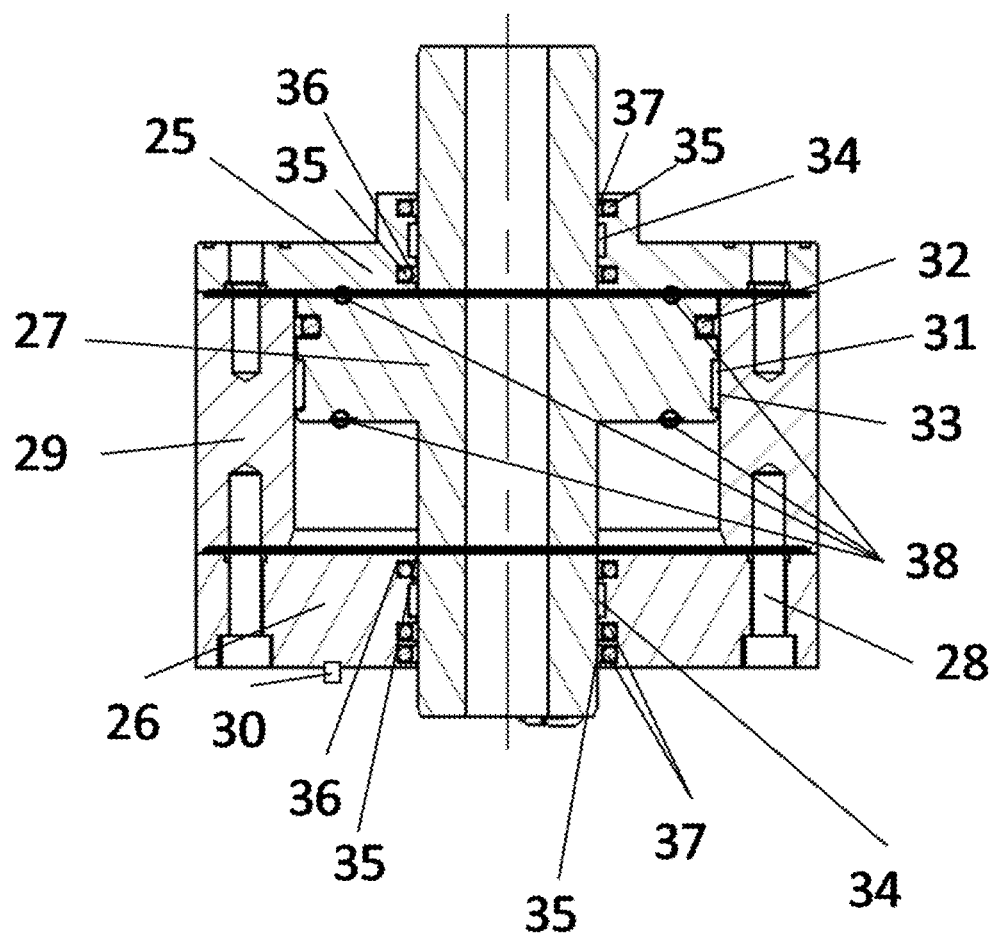
Figure 3C:
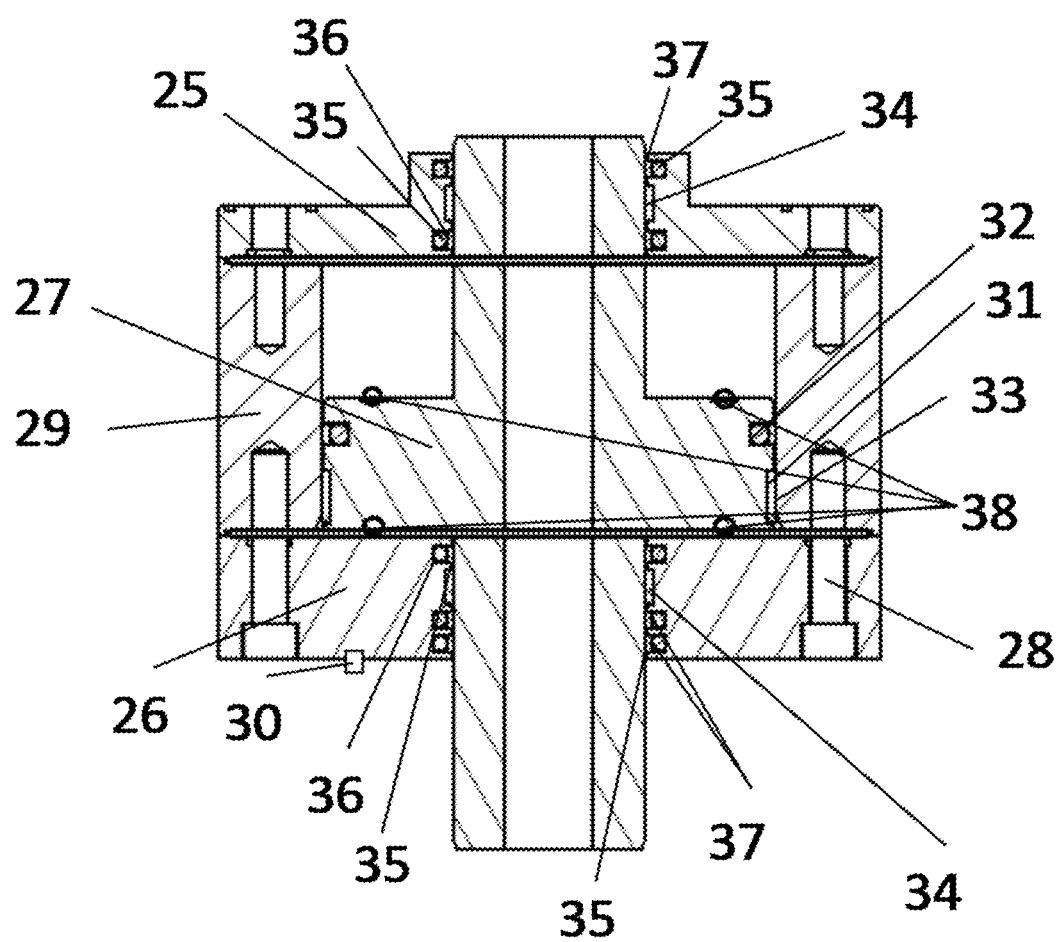
Figure 4A:
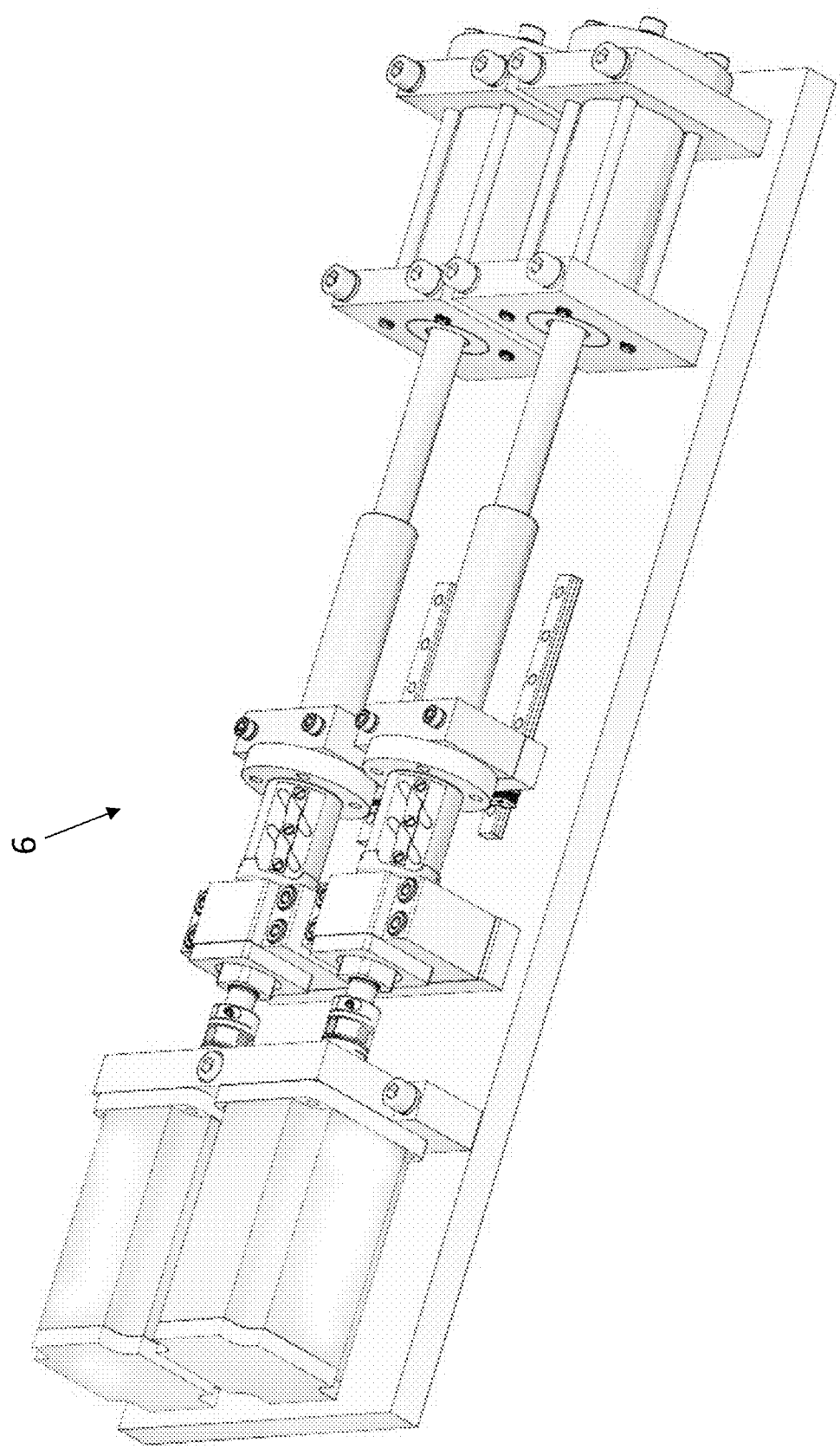
Figure 4B:
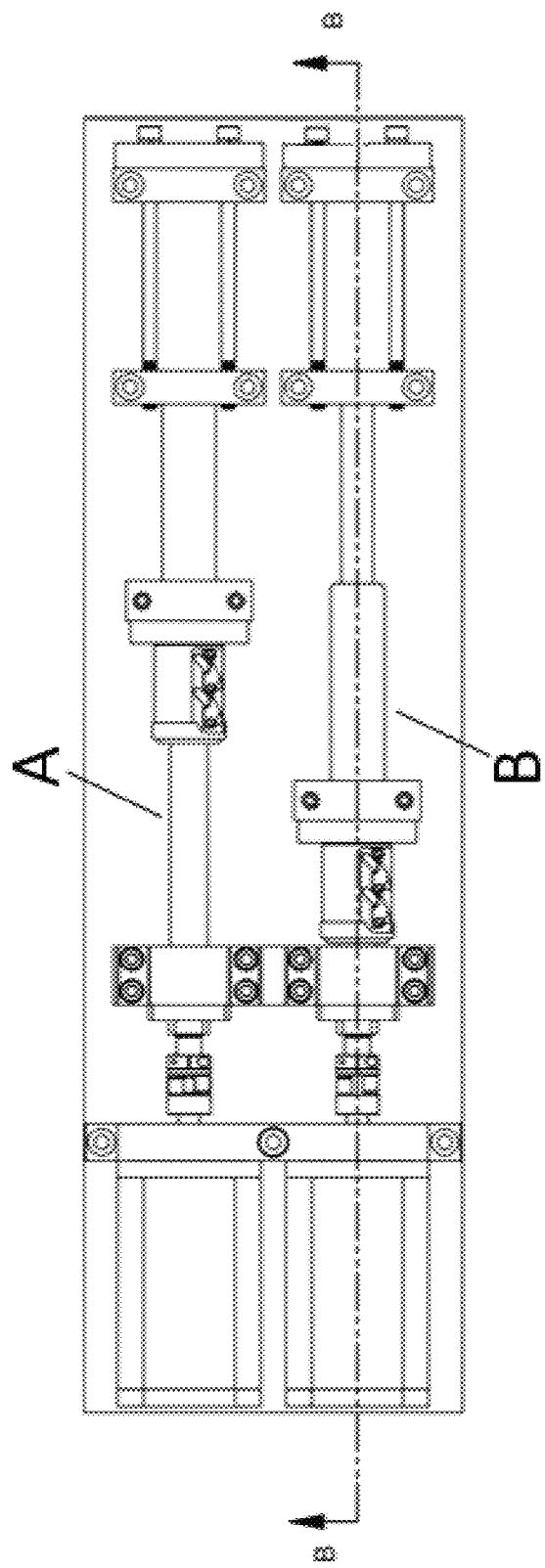
Figure 4C:
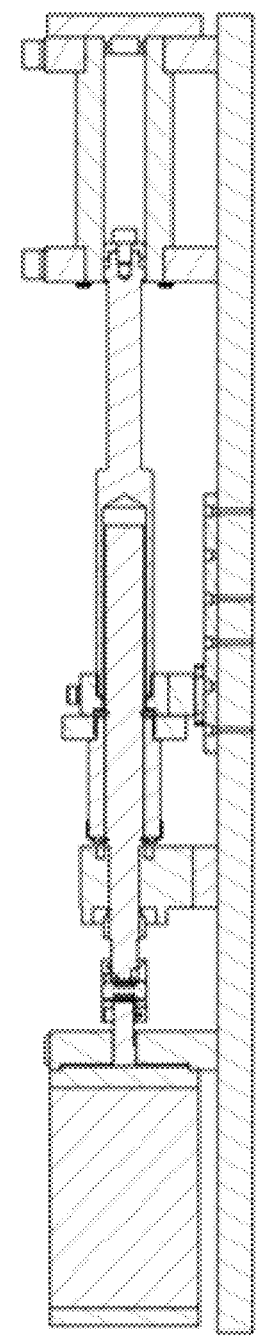

FIGS. 3A-3C show the components of a built-in actuator 2 that is sealed and capable of applying independent pressure inside the high-pressure chamber according to an embodiment that may have certain advantages such as elimination of the need to seal any surcharge actuator rod placed outside the chamber while imposing on the sediment, and compactness and reliability of the design compared to the use of water pressure difference between the sealed surcharge plate and the sediment. The actuator may consist of a surcharge actuator top cap 25, surcharge actuator bottom cap 26, surcharge actuator piston 27, fixing bolts 28, surcharge actuator tube 29, oil connector 30, piston seal O-ring 31, piston seal 32, piston guide ring 33, guide ring 34, rod seal O-ring 35, primary rod seal 36, secondary rod seal 37 and sealing O-ring 38. FIG. 3B is a cross section through the central axis of the actuator 2 of FIG. 3A with the actuator in a raised position. FIG. 3C is a cross section through the central axis of the actuator 2 of FIG. 3A with the actuator in a lowered position. All components (with the exception of bolts 28) of FIG. 3A are also represented in FIG. 3B and FIG. 3C, with sealing O-rings 38 displayed in front of the cross section and passing across the body of surcharge actuator piston 27. Oil connector 30 is partially hidden in FIG. 3B and completely hidden by surcharge actuator piston 27 in FIG. 3C.

The built-in actuator 2 can impose loading and unloading by retraction and extension of the surcharge actuator piston 27 as shown in FIG. 3B and FIG. 3C. In the case of gas production through the wellbore 7, the hollow design of the actuator piston would allow imposing a surcharge loading (e.g., up to 3 MPa surcharge, which is typical for sediment depths found in marine settings) on the sediment without loading the wellbore 7, similar to certain field usage case scenarios. Embodiments can simulate shallow depth gas hydrate accumulations of up to 50 m by solely the elevated gravity field of the centrifuge as well as deep gas hydrate accumulations of up to 400 m by using the surcharge loading actuator in conjunction with the elevated gravity field of the centrifuge. Unlike the proprietary devices, which simulate the isotropic stress or one-dimensional surcharge loading on the sediment at 1-g (without elevated gravity), the CEHC 1 can simulate the stress gradient in depth resulting in a load distribution with the depth on the wellbore 7 casing. Furthermore, a free moving design of the wellbore 7 casing can simulate the relative settlement of the casing and sediment and the induced axial loads may be measured by the strain gauges on the wellbore casing. During the depressurization of the wellbore from the initial pressure (e.g., from 10 MPa to 0.5 MPa) 7, the continuous flux high-pressure pumps 6 operate to keep the pressure at boundaries constant while simulating the localized pressure drop and the dissociation of gas hydrates in the vicinity of the wellbore. In certain embodiments, the flow rate of the pump varies as a function of the pressure that is required to be maintained.

FIGS. 4A-4E shows a continuous flux high-pressure pump 6 of the CEHC 1 in accordance with an embodiment of the subject invention. The continuous high-pressure water flux may be achieved by using two or more parallel syringe pumps, in which pump B extracts (section B-B) and fills with water while pump A extends (section C-C) and generates pressure. Then the process is reverted resulting in a continuous flux of high-pressure water supply. One advantage of this design is the continuous inflow of water at required pressures and flow rates. By use of additional parallel pump(s), the system may be made more versatile and robust. While beneficially supplying a continuous high-pressure water flow, the syringe pumps 6 are advantageously configured and adapted to operate at an elevated gravity of the centrifuge.

Another feature of the subject invention is the simulation of the working load on the offshore structures within the gas hydrate-bearing sediments. Following the hydrate formation inside the sediment by generating favorable thermodynamic conditions of temperature and pressure, a pre-installed offshore structure such as gravity-based structures, tension-leg platforms and spar platforms can be loaded to the working load by the built-in actuator. It is followed by subjecting the offshore structure to heating and cooling cycles, pore pressure changes, phase change, and cyclic axial loads. The settlement and induced loads on the offshore structure may advantageously be measured using systems and methods of the subject invention.

Another feature of certain embodiments of the subject invention is the simulation of the $CO_2$ sequestration through direct $CO_2$ injection as well as $CO_2$—$CH_4$ exchange in the centrifuge. The geotechnical centrifuge can reduce the time required to model years-long processes of $CO_2$ sequestration and the long-term hydro-mechanical responses of the reservoir. This can be achieved by scaling the required time for time-dependent phenomena that are heavily involved in reservoir response such as gas/water transport, heat conduction, convection and consolidation of the sediment by imposing an enhanced gravitational acceleration to the model in the centrifuge. As an example, at the centrifuge tests of 40 g (i.e., N=40), the capacity of the chamber would be 6,400 $m^3$ and the thickness of the simulated sediment would be 27 m thick in the prototype. In certain embodiments, mass and heat flows may occur 1600 times faster in the model compared to the prototype.

In order that the present disclosure may be more readily understood, certain terms are defined below, and throughout the detailed description, to provide guidance as to their meaning as used herein.

As used herein, the terms "a," "an," "the" and similar terms used in the context of the present invention are to be construed to cover both the singular and plural unless otherwise indicated herein or clearly contradicted by the context. Thus, for example, reference to "an arm" or "a hole" should be construed to cover or encompass both a singular arm or a singular hole and a plurality of arms and a plurality of holes, unless indicated otherwise or clearly contradicted by the context.

As used herein, the terms "about" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, the term "and/or" should be understood to mean "either or both" of the features so conjoined, i.e., elements that are conjunctively present in some cases and disjunctively present in other cases.

As used herein, the terms "comprising", "consisting of" and "consisting essentially of" are defined according to their standard meaning. The terms may be substituted for one another herein in order to attach the specific meaning associated with each term.

As used herein, the term "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Materials and Methods

All patents, patent applications, provisional applications, and publications referred to or cited herein are incorporated by reference in their entirety, including all figures and tables, to the extent they are not inconsistent with the explicit teachings of this specification.

The present disclosure is to be considered as an exemplification of the invention and is not intended to limit the invention to the specific embodiments illustrated by the figures or description below.

Example 1

A specific exemplary and non-limiting embodiment may provide a CEHC for a scaled gas production simulation at 1000 m³ of gas per day, consisting of a high-pressure chamber 1 to sustain 100 atmospheres pressure for hydrate formation inside the sand sediment 14; high-pressure syringe pumps 6 having a bore of 20 mm and a stroke of 150 mm, to generate the required pore pressures of 120 atmospheres for hydrate formation as well as sustaining the pressure at the boundaries, requiring 80 atmospheres pressure at 2 liters per minute flow rate during dissociation and pressure transducers 12 at the boundaries to measure the water pressure in the range of 0-120 atmospheres and gas pressure in the range of 0-120 atmospheres from gas cylinder 16; an 4000 Watt at 0° C. cooling system comprising built-in cooling coil 4 inside the high-pressure chamber and a circulating bath 13 outside the chamber to sustain the temperatures for hydrate formation and stability in the range of 0-4 degrees Celsius; 4) a built-in 2 MPa actuator 2 and 300 mm diameter by 150 mm stroke surcharge plate 3 to simulate the surcharge loading; a back pressure control 8 and N2 gas cylinder 15 to control the pressure inside the wellbore 7 in the range of 0-120 atmospheres, a 1000 watt heating element on the wellbore, 10 liter per min water gas separation system 9, and flow measurement systems for gas 10 (0-100 standard liter per min) and for water 11 (10 liter per min).

EXEMPLIFIED EMBODIMENTS

The invention may be better understood by reference to certain illustrative examples, including but not limited to the following:

Embodiment 1. A centrifuge energy harvesting chamber (CEHC) comprising:
    a high-pressure chamber configured to sustain sufficient pressure and temperature for hydrate formation within a sediment bed in an operating centrifuge,
    one or more high-pressure pumps configured to sustain sufficient pore pressure and boundary pressure for hydrate formation around the sediment bed,
    a cooling system comprising a built-in cooling coil configured to cool the sediment bed inside the high-pressure chamber,
    a built-in actuator configured to provide an activation force acting within the high-pressure chamber, and
    a surcharge plate to configured to simulate surcharge loading on the sediment bed when acted upon by the activation force.

Embodiment 2. The CEHC of Embodiment 1, wherein the one or more high-pressure pumps comprise a pair of syringe pumps.

Embodiment 3. The CEHC of Embodiment 2, wherein the pair of syringe pumps are configured for repeated sequential operation to provide a continuous high-pressure fluid flow at an elevated gravity of the centrifuge.

Embodiment 4. The CEHC of Embodiment 1, further comprising a backpressure control system comprising an inert gas source configured to control the pressure inside the wellbore.

Embodiment 5. The CEHC of Embodiment 1, further comprising a water/gas separation system, a gas flow measurement system configured to measure a flow of gas, and a water flow measurement system configured to measure a flow of water.

Embodiment 6. The CEHC of Embodiment 1, the cooling system further comprising a circulating heat exchanger outside the high-pressure chamber and configured to selectively sustain the required temperatures for hydrate formation or hydrate stability, respectively.

Embodiment 7. The CEHC of Embodiment 1, further comprising a high-pressure linear variable displacement transducer (LVDT) configured to measure settlement within the sediment bed.

Embodiment 8. The CEHC of Embodiment 1, wherein the CEHC is securely fastened to the centrifuge and sufficiently sealed and insulated to operate as an adiabatic system.

Embodiment 9. The CEHC of Embodiment 1, wherein the CEHC further comprises an instrumentation module, sensors, and software configured to continuously measure one or more of temperature, pressure, pumping rate, and wellbore pressure while the centrifuge is in-flight.

Embodiment 10. The CEHC of Embodiment 4, wherein the inert gas source comprises a N2 gas cylinder.

Embodiment 11. The CEHC of Embodiment 7, wherein the high-pressure LVDT is configured to measure settlement of a simulated seabed and one of more offshore structures within the sediment bed.

Embodiment 12. A method of gas production simulation, the method comprising the following steps:
    providing, within an operating centrifuge, a centrifuge energy harvesting chamber (CEHC) comprising:
    a high-pressure chamber,
    a sediment bed within the high-pressure chamber,
    a high-pressure pump operably connected to the high-pressure chamber,
    a cooling system operably connected to the high-pressure chamber,
    an actuator configured to provide an activation force, and
    a surcharge plate to configured to simulate surcharge loading on the sediment bed when acted upon by the activation force;
    creating a centrifugal loading by operation of the centrifuge;
    pressurizing, by the high-pressure pump, the sediment bed within the high-pressure chamber to a first pressure sufficient for gas hydrate formation or maintenance;
    cooling, by the cooling system, the sediment bed within the high-pressure chamber to a first temperature sufficient for gas hydrate formation at the first pressure;
    forming or maintaining gas hydrates within the sediment bed under centrifugal loading;
    performing, within the sediment bed and under the centrifugal loading, a simulation of hydrate dissociation, wellbore casing deformation, or seabed subsidence during gas production from hydrate-bearing soils.

Embodiment 13. The method of Embodiment 12, wherein the high-pressure pump comprises a pair of syringe pumps and the step of pressurizing, by the high-pressure pump, the sediment bed within the high-pressure chamber comprises repeated sequential operation of the pair of syringe pumps to provide a continuous high-pressure fluid flow at an elevated gravity of the centrifuge.

Embodiment 14. The method of Embodiment 12, the provided CEHC further comprising a backpressure control system comprising an inert gas source and configured to control the pressure inside the wellbore.

Embodiment 15. The method of Embodiment 12, the provided CEHC further comprising:
- a water/gas separation system;
- a set of sensors comprising at least one sensor selected from the group containing:
  - a temperature sensor,
  - a pressure sensor,
  - a gas flow measurement system configured to measure a flow of gas,
  - a water flow measurement system configured to measure a flow of water, and
  - a high-pressure linear variable displacement transducer (LVDT) configured to measure settlement within the sediment bed; and
- an instrumentation module configured to monitor at least one sensor from the set of sensors while the centrifuge is in-flight.

Embodiment 16. The method of Embodiment 15, the instrumentation module further comprising:
- a processor in operable communication with at least one sensor from the set of sensors, and
- a non-transitory machine-readable medium in operable communication with the processor and having instructions stored thereon that, when executed by the processor, report or record at least one value correlated to temperature, pressure, pumping rate, or wellbore pressure.

Embodiment 17. The method of Embodiment 16, wherein the provided CEHC is securely fastened to the centrifuge and sufficiently sealed and insulated to operate as an adiabatic system.

Embodiment 18. A centrifuge energy harvesting chamber (CEHC) system comprising:
- a centrifuge,
- a high-pressure chamber mounted to the centrifuge,
- a sediment bed within the high-pressure chamber,
- a high-pressure pump comprising a multiplicity of syringe pumps, the high pressure pump operably connected to the high-pressure chamber and configured for repeated sequential operation of the multiplicity of syringe pumps to provide a continuous high-pressure fluid flow at an elevated gravity of the centrifuge,
- a cooling system operably connected to the high-pressure chamber,
- an actuator configured to provide an activation force, and
- a surcharge plate to configured to simulate surcharge loading on the sediment bed when acted upon by the activation force;

Embodiment 19. The CEHC system of Embodiment 18, further comprising a backpressure control system comprising an inert gas source and configured to control the pressure inside the wellbore.

Embodiment 20. The CEHC system of Embodiment 19, further comprising at least one seal and at least one insulating member configured to allow operation of the CEHC as an adiabatic system while the centrifuge is in-flight.

Embodiment 21. A centrifuge energy harvesting chamber (CEHC) comprising: A high-pressure chamber of suitable strength to be used in a centrifuge to sustain the required pressure and temperature for hydrate formation inside the sediment, one or more high-pressure syringe pumps configured to generate the required pore pressures for hydrate formation as well as sustaining the required pressure at the boundaries, a cooling system comprising a built-in cooling coil inside the high-pressure chamber, a built-in actuator and surcharge plate to simulate surcharge loading.

Embodiment 22. The CEHC of Embodiment 21, further comprising backpressure control and an N2 gas cylinder to control the pressure inside the wellbore.

Embodiment 23. The CEHC of Embodiment 21, further comprising a water/gas separation system, a flow measurement system configured to measure a flow of gas and a flow measurement system configured to measure a flow of water.

Embodiment 24. The CEHC of Embodiment 1, further comprising a circulating bath outside the chamber to configured to selectively sustain the required temperatures for hydrate formation and hydrate stability, respectively.

Embodiment 25. The CEHC of Embodiment 21, further comprising a high-pressure linear variable displacement transducer (LVDT) configured to measure settlement of a seabed and one of more offshore structures.

Embodiment 26. The CEHC of Embodiment 21, wherein the CEHC is securely fastened to the centrifuge and sufficiently sealed and insulated to operate as an adiabatic system.

Embodiment 27. The CEHC of Embodiment 21, wherein the CEHC further comprises an instrumentation module, sensors, and software configured to continuously measure one or more variables relevant to the temperature, pressure, pumping rate, and the wellbore pressure while the centrifuge is in-flight.

Although the present invention has been illustrated and described herein with reference to preferred embodiments and specific examples thereof, it will be readily apparent to those of ordinary skill in the art that other embodiments and examples may perform similar functions and/or achieve like results.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A centrifuge energy harvesting chamber (CEHC) comprising:
   - a high-pressure chamber configured to sustain sufficient pressure and temperature for hydrate formation within a sediment bed in an operating centrifuge,
   - one or more high-pressure pumps configured to sustain sufficient pore pressure and boundary pressure for hydrate formation around the sediment bed,
   - a cooling system comprising a cooling coil inside the high-pressure chamber configured to cool the sediment bed inside the high-pressure chamber,
   - an actuator configured to provide an activation force acting within the high-pressure chamber, and
   - a surcharge plate to configured to load the sediment bed when acted upon by the activation force.

2. The CEHC of claim 1, wherein the one or more high-pressure pumps comprise a pair of syringe pumps.

3. The CEHC of claim 2, wherein the pair of syringe pumps are configured for repeated sequential operation to provide a continuous high-pressure fluid flow at an elevated gravity of the centrifuge.

4. The CEHC of claim 1, further comprising a backpressure control system comprising an inert gas source configured to control a pressure inside a wellbore.

5. The CEHC of claim 1, further comprising a water gas separation system configured to produce a flow of gas and a flow of water, a gas flow measurement system configured to measure the flow of gas, and a water flow measurement system configured to measure the flow of water.

6. The CEHC of claim 1, the cooling system further comprising a circulating heat exchanger outside the high-pressure chamber and configured to selectively sustain the required temperatures for hydrate formation or hydrate stability, respectively.

7. The CEHC of claim 1, further comprising a high-pressure linear variable displacement transducer (LVDT) configured to measure settlement within the sediment bed.

8. The CEHC of claim 1, wherein the CEHC is securely fastened to the centrifuge and sufficiently sealed and insulated to operate as an adiabatic system.

9. The CEHC of claim 1, wherein the CEHC further comprises an instrumentation module, sensors, and software configured to continuously measure one or more of temperature, pressure, pumping rate, and wellbore pressure while the centrifuge is in-flight.

10. The CEHC of claim 4, wherein the inert gas source comprises a $N_2$ gas cylinder.

11. The CEHC of claim 7, wherein the high-pressure LVDT is configured to measure settlement of a simulated seabed and one of more offshore structures within the sediment bed.

12. A method of gas production simulation, the method comprising the following steps:
  providing, within an operating centrifuge, a centrifuge energy harvesting chamber (CEHC) comprising:
    a high-pressure chamber,
    a sediment bed within the high-pressure chamber,
    a high-pressure pump operably connected to the high-pressure chamber,
    a cooling system operably connected to the high-pressure chamber,
    an actuator configured to provide an activation force, and
    a surcharge plate to configured to load the sediment bed when acted upon by the activation force;
  creating a centrifugal loading by operation of the centrifuge;
  pressurizing, by the high-pressure pump, the sediment bed within the high-pressure chamber to a first pressure sufficient for gas hydrate formation or maintenance;
  cooling, by the cooling system, the sediment bed within the high-pressure chamber to a first temperature sufficient for gas hydrate formation or maintenance at the first pressure;
  forming or maintaining gas hydrates within the sediment bed under centrifugal loading;
  performing, within the sediment bed and under the centrifugal loading, a simulation of hydrate dissociation, wellbore casing deformation, or seabed subsidence during gas production from hydrate-bearing soils.

13. The method of claim 12, wherein the high-pressure pump comprises a pair of syringe pumps and the step of pressurizing, by the high-pressure pump, the sediment bed within the high-pressure chamber comprises repeated sequential operation of the pair of syringe pumps to provide a continuous high-pressure fluid flow at an elevated gravity of the centrifuge.

14. The method of claim 12, the provided CEHC further comprising a backpressure control system comprising an inert gas source and configured to control a pressure inside a wellbore.

15. The method of claim 12, the provided CEHC further comprising:
  a water gas separation system configured to produce a flow of gas and a flow of water;
  a set of sensors comprising at least one sensor selected from the group containing:
    a temperature sensor,
    a pressure sensor,
    a gas flow measurement system configured to measure the flow of gas,
    a water flow measurement system configured to measure the flow of water, and
    a high-pressure linear variable displacement transducer (LVDT) configured to measure settlement within the sediment bed; and
  an instrumentation module configured to monitor at least one sensor from the set of sensors while the centrifuge is in-flight.

16. The method of claim 15, the instrumentation module further comprising:
  a processor in operable communication with at least one sensor from the set of sensors, and
  a machine-readable medium in operable communication with the processor and having instructions stored thereon that, when executed by the processor, report or record at least one value correlated to temperature, pressure, pumping rate, or wellbore pressure.

17. The method of claim 16, wherein the provided CEHC is securely fastened to the centrifuge and sufficiently sealed and insulated to operate as an adiabatic system.

18. A centrifuge energy harvesting chamber (CEHC) system comprising:
  a centrifuge,
  a high-pressure chamber mounted to the centrifuge,
  a sediment bed within the high-pressure chamber,
  a high-pressure pump comprising a multiplicity of syringe pumps, the high pressure pump operably connected to the high-pressure chamber and configured for repeated sequential operation of the multiplicity of syringe pumps to provide a continuous high-pressure fluid flow at an elevated gravity of the centrifuge,
  a cooling system operably connected to the high-pressure chamber,
  an actuator configured to provide an activation force, and
  a surcharge plate to configured to load the sediment bed when acted upon by the activation force.

19. The CEHC system of claim 18, further comprising a backpressure control system comprising an inert gas source and configured to control a pressure inside a wellbore.

20. The CEHC system of claim 19, further comprising at least one seal and at least one insulating member configured to allow operation of the CEHC as an adiabatic system while the centrifuge is in-flight.

* * * * *